US007056492B2

(12) United States Patent
Goudie et al.

(10) Patent No.: US 7,056,492 B2
(45) Date of Patent: Jun. 6, 2006

(54) *MYCOPLASMA HYOPNEUMONIAE* VACCINE AND METHODS FOR REDUCING *MYCOPLASMA BOVIS* PNEUMONIA IN CATTLE

(75) Inventors: Alexander C. Goudie, Old Saybrook, CT (US); Andrew Raymond Peters, Ledyard, CT (US); Robin Lee Keich, Waterford, CT (US)

(73) Assignee: Pfizer Inc., New York, NY (US)

( * ) Notice: Subject to any disclaimer, the term of this patent is extended or adjusted under 35 U.S.C. 154(b) by 47 days.

(21) Appl. No.: 10/177,860

(22) Filed: Jun. 20, 2002

(65) Prior Publication Data

US 2003/0064079 A1 Apr. 3, 2003

Related U.S. Application Data

(60) Provisional application No. 60/302,586, filed on Jul. 2, 2001.

(51) Int. Cl.
*A61K 49/00* (2006.01)
*A61K 39/00* (2006.01)
*A01N 63/00* (2006.01)

(52) U.S. Cl. ........................ 424/9.2; 424/9.1; 424/93.1; 424/93.4; 424/184.1; 424/234.1; 424/264.1; 435/243; 435/870

(58) Field of Classification Search .................. 424/9.1, 424/9.2, 93.1, 93.4, 184.1, 234.1, 264.1; 435/243, 870
See application file for complete search history.

(56) References Cited

U.S. PATENT DOCUMENTS 5,565,205 A 10/1996 Petersen et al.
5,788,962 A 8/1998 McIntosh et al.

FOREIGN PATENT DOCUMENTS

WO WO 91 15593 A 10/1991

OTHER PUBLICATIONS

Tarasiuk, K., et al., Efficacy of Immunoprophylaxis in the Control of Mycoplasmal Pneumonia of Swine, Medycyna Weterynaryjna, vol. 48, No. 9, 1992, pp. 402–405.

*Primary Examiner*—Rodney P Swartz
(74) *Attorney, Agent, or Firm*—Timothy J. Gumbleton; Thomas A. Wootton

(57) ABSTRACT

The present invention relates to methods for treating or preventing a disease or disorder in an animal caused by infection by *Mycoplasma bovis* (*M. bovis*) by administering to the animal an effective amount of a *Mycoplasma hyopneumoniae* (*M. hyo*) vaccine. The *M. hyo* vaccine can be a whole or partial cell inactivated or modified live preparation, a subunit vaccine, or a nucleic acid or DNA vaccine. The *M. hyo* vaccine administered in accordance with the present invention can be synthesized or recombinantly produced.

25 Claims, 1 Drawing Sheet

*MYCOPLASMA HYOPNEUMONIAE* VACCINE AND METHODS FOR REDUCING *MYCOPLASMA BOVIS* PNEUMONIA IN CATTLE

FIELD OF THE INVENTION

The present invention relates to methods for treating or preventing a disease or disorder in an animal caused by infection by *Mycoplasma bovis* (*M. bovis*) by administering to the animal an effective amount of a *Mycoplasma hyopneumoniae* (*M. hyo*) vaccine. The *M. hyo* vaccine can be a whole or partial cell inactivated or modified live preparation, a subunit vaccine, or a nucleic acid or DNA vaccine. The *M. hyo* vaccine administered in accordance with the present invention can be synthesized or recombinantly produced.

BACKGROUND OF THE INVENTION

*M. bovis* is a bovine pathogen in housed or intensively reared beef and dairy cattle. The most frequently reported clinical manifestation is pneumonia of calves, which is often accompanied by arthritis, also known as pneumonia-arthritis syndrome. Its etiological role has also been associated with mastitis, otitis, and reproductive disease or disorders of cows and bulls. Significant economic losses are linked with *M. bovis* induced respiratory disease, since *M. bovis* has been associated with up to 36% of the mortality due to bovine respiratory disease (BRD). In order to reduce mortality, antibiotic therapy is often used since no fully licensed vaccines are currently available. Prevention of *M. bovis* disease may also reduce predisposition of the animal to other respiratory diseases. Therefore, there is a need to develop efficacious and safe vaccines against *M. bovis*. *M. hyo* is a bacterial pathogen that causes enzootic pneumonia in swine. The majority of known vaccines against *M. hyo* are based on inactivated whole cell preparations of *M. hyo*. Other vaccines against *M. hyo* include subunit vaccines composed of *M. hyo* derived proteins, polypeptides or immunogenic fragments of such proteins or polypeptides, and DNA vaccines composed of DNA encoding for one or more *M. hyo* derived proteins or polypeptides and immunogenic fragments thereof.

Examples of whole cell inactivated *M. hyo* vaccines include chemically inactivated whole cell cultures with *M. hyo*, coupled with an oil adjuvant (RESPISURE® and STELLAMUNE™) commercially available from Pfizer Inc., USA.

A number of *M. hyo* proteins have been described. International Patent Publication WO 96/28472 describes six protein antigen species of *M. hyo* at molecular weights of 46–48, 52–54, 60–64, 72–75, 90–94 and 110–114 kilodaltons, and discloses partial protein sequences of the 52–54, 60–64 and 72–75 kilodalton antigens and the full length nucleotide and amino acid sequences of the 46–48 kilodalton antigen.

The cloning of the gene encoding the *M. hyo* protein P46, i.e. p46, was also described by Futo et al. in *J. Bacteriol* 177:1915–1917(1995) and further in European Patent Publication No. 0 475 185 A1.

Wise and Kim (1987, *J. Bacteriol.* 169: 5546–5555) reported four integral membrane protein species in *M. hyo*, named p70, p65 (P65, supra), p50 and p44, the latter three of which are modified by covalent lipid attachments and induce a strong humoral immune response. The protective effects of the immune response were not investigated. The gene encoding the P65 protein has been cloned, and its sequences and uses in vaccines and diagnostics are described in U.S. Pat. No. 5,788,962.

International Patent Publication WO 91/15593 describes five proteins of *M. hyo* of apparent molecular weights of 105, 90, 85, 70 and 43 kilodaltons. A full-length sequence of the gene encoding 85 kilodalton protein (protein C) was provided, as were partial nucleotide sequences encoding the other four proteins.

U.S. Pat. No. 5,252,328 to Faulds discloses amino terminal sequences of immunoreactive *M. hyo* proteins, the molecular weights of which are 36, 41, 44, 48, 64, 68, 74.5, 79, 88.5, 96 and 121 kilodaltons. Other proteins identified based on the electrophoretic mobilities but for which no protein sequences were disclosed had apparent molecular weights of 22.5, 34 and 52 kilodaltons. While U.S. Pat. No. 5,252,328 proposed the use of these proteins in vaccine formulations against *M. hyo* infections, no results of vaccine trials were reported.

International Patent Publication WO 95/09870 discloses biochemical methods for the purification of *M. hyo* adhesins, the mycoplasmal integral membrane proteins responsible for adhesion to the cilia of the host's upper respiratory epithelium. WO 95/09870 also proposes assays and uses for these proteins, for example in vaccines and diagnostics.

A research paper by King et al. (1997; *Vaccine* 15:25–35) disclosed Mhp1, a 124 kilodalton adhesin that is a strain variant of P97.

A 94 kilodalton variant of P97 was identified by Wilton et al. (1998, *Microbiology* 144:1931–1943). Additionally, the p97 gene was shown to be part of an operon that also encodes a second protein, termed P102, of a predicted molecular weight of approximately 102 kilodaltons (Hsu et al., 1998, *Gene* 214:13–23). Minion and Hsu suggest the use of P102 in vaccines against *M. hyo* infections in the international patent publication WO 99/26664 but do not report vaccine trials.

Prior to the present invention, there has been no recognition that a *M. hyo* vaccine can provide protective effects in cattle against disorders caused by *M. bovis*.

SUMMARY OF THE INVENTION

The present invention provides a method of treating or preventing a disease or disorder in an animal caused by infection with *M. bovis* comprising administering to the animal, an effective amount of a *M. hyo* vaccine.

The present invention further provides a method that provides protection to animals such as dairy cattle, in particular, bovine, against pneumonia, for example, preventing and reducing lung lesions.

The present invention further provides a method of vaccination using a *M. hyo* vaccine that provides increased immunocompetence to calves and thereby increased resistance to other BRD pathogens, e.g., decreased predisposition to infection and disease caused by, but not limited to, but not limited to, bovine herpesvirus type 1 (BHV-1), bovine viral diarrhea virus (BVDV), bovine respiratory syncitial virus (BRSV), parainfluenza virus (PI3), *Pasteurella multocida, Haemophilus somnus, Mycoplasma mycoides, Mycoplasma agalactiae, Mycoplasma californicum, Mycoplasma bovirhinis, Mycoplasma dispar, Mycoplasma canis,* and *Manheimia haemolytica*. The present invention also encompasses a *M. hyo* vaccines and methods of eradicating *Mycoplasma bovis* from infected herds by administering to an animal an effective amount of a *M. hyo* vaccine and a pharmaceutically acceptable carrier.

The *M. hyo* vaccine employed in the present methods can be a whole or partial cell preparation (e.g., a bacterin or modified live preparation), a subunit vaccine (e.g., a subunit vaccine composed of a *M. hyo* derived proteins, polypeptides or immunogenic fragments thereof), a DNA vaccine (e.g., a DNA encoding a *M. hyo* derived proteins, polypeptides or an immunogenic fragment thereof). The *M. hyo* polypeptides, proteins, immunogenic fragments thereof and genes or nucleic acids provided in the *M. hyo* vaccine can be synthesized or recombinantly produced using techniques known in art.

The *M. hyo* vaccine administered in accordance with the present invention may include additional components, such as an adjuvant and optionally a second or more antigens for use in a combination vaccine. A second antigen is selected from the following, including but not limited to bovine herpesvirus type 1 (BHV-1), bovine viral diarrhea virus (BVDV), bovine respiratory syncitial virus (BRSV), parainfluenza virus (PI3), *Pasteurella multocida, Haemophilus somnus, Mycoplasma mycoides, Mycoplasma agalactiae, Mycoplasma californicum, Mycoplasma bovirhinis, Mycoplasma dispar, Mycoplasma canis,* and *Manheimia haemolytica.*

DETAILED DESCRIPTION OF THE INVENTION

Figure 1:
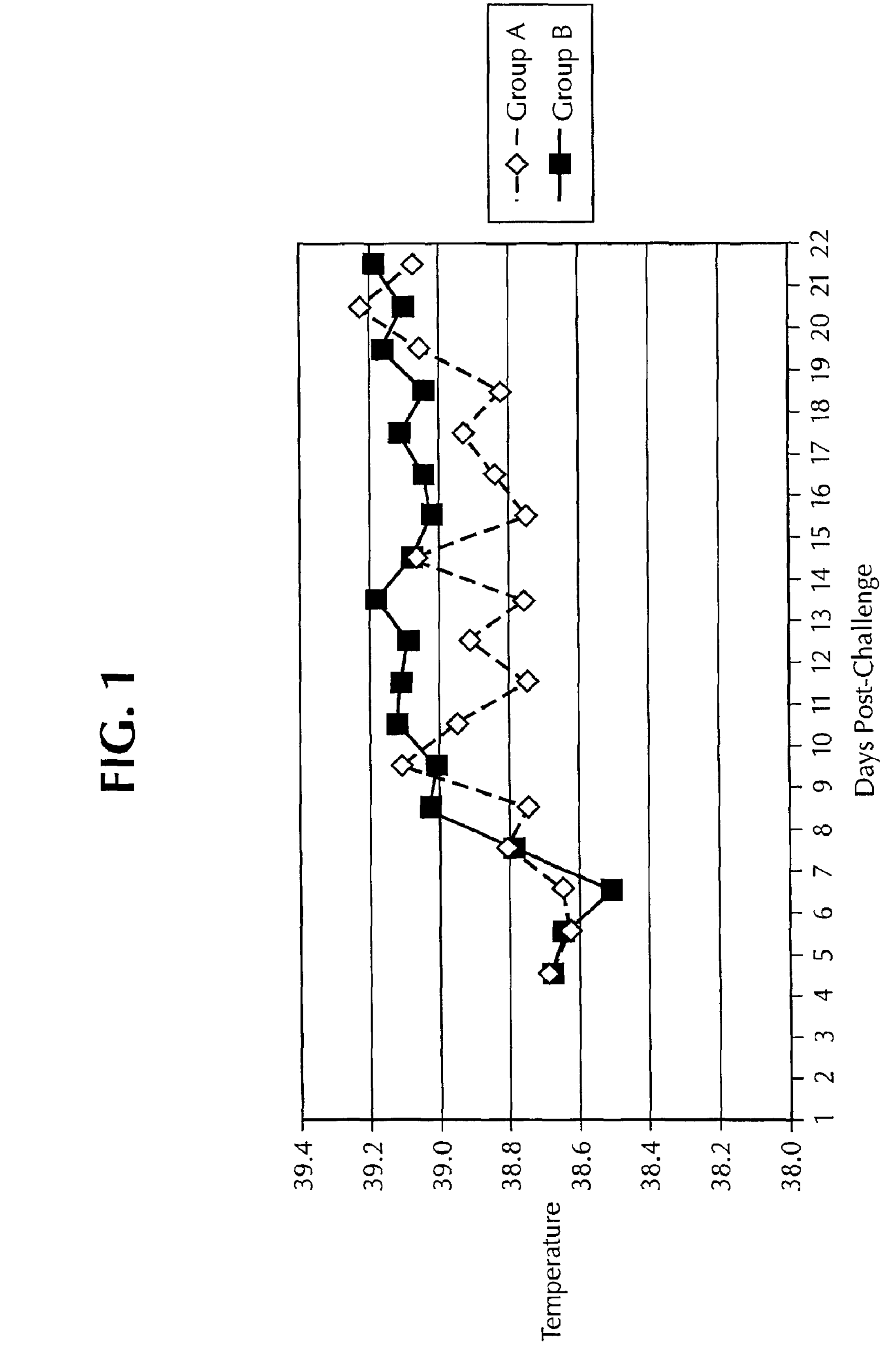
FIG. 1 depicts the mean body temperatures of calves immediately prior to and following experimental *M. bovis* challenge. Calves in Group A were vaccinated with two doses of *M. hyo* bacterin prior to the challenge. Calves in Group B were vaccinated with placebo prior to the challenge.

The present invention provides a method of treating or preventing a disease or disorder in an animal caused by infection with *M. bovis* by administering to the animal, an effective amount of a *M. hyo* vaccine.

In certain embodiments, the vaccines used in the method of the present invention comprise a partial or whole cell *M. hyo* inactivated preparation (bacterin) or modified live vaccine and a pharmaceutically acceptable carrier, or partial or whole cell *M. hyo* inactivated preparation (bacterin) or modified live vaccine and an adjuvant.

In other specific embodiments, the vaccines used in the method of the present invention comprise an immunogenic protein or polypeptide or fragment thereof and a pharmaceutically acceptable carrier, or an immunogenic protein or polypeptide or fragment thereof and an adjuvant.

For clarity of disclosure, and not by way of limitation, the detailed description of the invention is divided into the following subsections which describe or illustrate certain features, embodiments or applications of the invention.

DEFINITIONS AND ABBREVIATIONS

The term "treating or preventing" with respect to a *M. bovis* infection as used herein means to inhibit the replication of *M. bovis* bacteria, to inhibit *M. bovis* shedding or transmission, or to prevent *M. bovis* from establishing itself in its host, and to alleviate the symptoms of the disease or disorder caused by *M. bovis* infection, or to accelerate the clearance of *M. bovis* bacteria from the animal host. The treatment is considered therapeutic if there is a reduction in bacterial load, decrease in pulmonary infections, reduced rectal temperatures, and/or increase in food uptake and/or growth. The method of the present invention is, for example, effective in preventing or reducing lung lesions, reducing rectal temperatures and reducing levels of *M. bovis* in the lung normally seen in *M. bovis* infections.

The present method of treating or preventing a *M. bovis* infection by administering a *M. hyo* vaccine is also referred to herein as a vaccination method.

The term "*M. hyo* vaccine" that may be used in the present method can include, for example, a inactivated whole or partial *M. hyo* cell preparation, modified live vaccines, a subunit vaccine having one or more *M. hyo* derived proteins, polypeptides, or immunogenic fragments of such proteins or polypeptides, or one or more *M. hyo* genes or nucleic acids encoding for one or more *M. hyo* derived proteins, polypeptides, or immunogenic fragments thereof, and which genes or nucleic acids are capable of being expressed in vivo in the animal. The *M. hyo* polypeptides, proteins, immunogenic fragments of such polypeptides and proteins, or *M. hyo* genes or nucleic acids can be synthesized or recombinantly produced using techniques known in the art. Preferably, the *M. hyo* vaccine used in the method of the present invention is a bacterin.

The term "immunogenic fragment" as used herein refers to a fragment of a protein from *M. hyo*, which is capable of inducing an immune response in a host animal. The immune response may comprise, without limitation, induction of cellular and/or humoral immunity.

The term "animal" as used herein refers to all non-human animals, including mammals.

The term "cattle" as used herein refers to bovine animals including but not limited to steer, bulls, cows, and calves. Preferably, the method of the present invention is applied to an animal which is a non-human mammal; most preferably, a calf.

The term "bacterin" as used herein refers to a preparation of inactivated whole or partial *M. hyo* cells suitable for use as a vaccine.

The term "immunologically effective amount" refers to an amount of *M. hyo* vaccine sufficient to elicit an immune response in the animal to which it is administered. The immune response may comprise, without limitation, induction of cellular and/or humoral immunity. An effective amount of *M. hyo* vaccine means, for example, that the bacterin prevents or reduces the severity of *mycoplasmal pneumonia.*

The term "adjuvant" as used herein, is a potentiator of the immune response.

The term "pharmaceutically acceptable carrier" refers to a carrier medium that does not interfere with the effectiveness of the biological activity of the active ingredient, is chemically inert and is not toxic to the subject to whom it is administered.

Inactivated (Partial or Whole Cell) and Modified Live Vaccines

Inactivated or modified live *M. hyo* vaccines for use in the method of the present invention can be prepared using a variety of methods which are known in the art.

For example, *M. hyo* bacterins can be prepared from *M. hyo* isolates. Numerous *M. hyo* isolates are known to those skilled in the art and are available from, e.g., the American Type Culture Collection, 10801 University Boulevard, Manassas, Va. 20110-2209. These include for example: ATCC nos, 25095, 25617, 25934, 27714, and 27715.

*M. hyo* isolates can also be obtained directly from infected porcine lung lesions using known techniques.

*M. hyo* isolates can be inactivated using a variety of known methods, e.g., treating the bacterial isolate with binary ethyleneimine (BEI) as described in U.S. Pat. No. 5,565,205, or inactivation with formalin, glutaraldehyde, heat, irradiation, BPL, or other inactivants known to the art.

In addition to inactivated bacterial isolates, a bacterin product can also include an appropriate amount of one or more commonly used adjuvants. Suitable adjuvants may include, but are not limited to: mineral gels, e.g., aluminum hydroxide; surface active substances such as lysolecithin; glycosides, e.g., saponin and saponin derivatives such as Quil A or GPI-0100; cationic surfactants, e.g. DDA (quaternary hydrocarbon ammonium halogenides, pluronic polyols; polyanions and polyatomic ions; polyacrylic acids, non-ionic block polymers, e.g., Pluronic F-127 (B.A.S.F., USA); Avridine and Rantidine; peptides; recombinant mutant labile toxins, e.g., leukotoxin (LT) or cholera toxin (CT); chemically bound or close proximity molecular transporters; mineral oils, e.g. Montanide ISA-50 (Seppic, Paris, France), carbopol, Amphigen (Hydronics, USA), Omaha, Nebr. USA, Alhydrogel, (Superfos Biosector, Frederikssund, Denmark) oil emulsions, e.g. an emulsion of mineral oil such as BayolF/Arlacel A and water, or an emulsion of vegetable oil, water and an emulsifier such as lecithin; alum, cholesterol cytokines and combinations of adjuvants. Polyatomic ions can also function as dispersing, thickening and anticaking agents which allow the vaccine to be resuspended as a mondisperse suspension after a prolonger period of settling. The adjuvant combinations may be presented in aqueous, encapsulated (controlled or delayed release) or microencapsulated forms. *M. hyo* bacterins suitable for use in the method of the present invention can also be obtained through various commercial sources. Such sources include but are not limited to: RESPIFEND (Fort Dodge, American Home Products), HYORESP (Merial Ltd), M+PAC (Schering Plough), PROSYSTEM M (Intervet), INGLEVAC M (Boehringer), RESPISURE (Pfizer Inc), and STELLAMUNE MYCOPLASMA (Pfizer Inc).

A preferred source of the *M. hyo* bacterin for use in the method of the present invention is RESPISURE, RESPISURE ONE, and STELLAMUNE MYCOPLASMA.

A particularly preferred source of *M. hyo* bacterin for use in the method of the present invention is RESPISURE (PFIZER INC.), containing strain NL1042.

Preferably, the strain NL1042 is inactivated with BEI and adjuvanted with a commercially available adjuvant, preferably, AMPHIGEN (Hydronics, USA). A preferred dose is about 2.0 ml. Preservatives conventionally used include merthiolate/EDTA. Vaccines are formulated as liquid dosage or presented in a solid dosage with the making up a soluble component or a microparticulate that is resuspended in a pharmaceutically acceptable diluent prior to use. Methods of preparing soluble components or microparticulates include, but are not limited to, biacervation, congelgation, spray drying, bubble syringes, precipitation, supercritical sovlation/encapsulation and lyophilization. A carrier may be added, preferably, PBS. Preparation of modified live vaccines, such as by attenuation of virulent strains by passage in culture, is known in the art.

Inactivated *M. hyo* isolates can also be combined with the following bacteria and viruses, including but not limited to, bovine herpesvirus type 1 (BHV-1), bovine viral diarrhea virus (BVDV), bovine respiratory syncitial virus (BRSV), parainfluenza virus (PI13), *Pasteurella multocida, Haemophilus somnus, Mycoplasma mycoides, Mycoplasma agalactiae, Mycoplasma californicum, Mycoplasma bovirhinis, Mycoplasma dispar, Mycoplasma canis,* and *Manheimia haemolytica.*

Subunit Vaccines

The method of the present invention can be practiced using subunit vaccines composed of purified *M. hyo* immunogenic proteins, polypeptides, or immunogenic fragments of such proteins and polypeptides. Such proteins and polypeptides can be prepared using techniques known in the art, for example extracts prepared using surface action agents, or thermal, chemical and mechanical extracts. Further, protein purity or homogeneity can be determined using methods which are well known to those skilled in the art, such as polyacrylamide gel electrophoresis followed by appropriate gel-staining, HPLC or other similar methods well known in the art.

In one embodiment, the subunit vaccine used in the present invention includes at least one *M. hyo* protein or polypeptide. Preferred *M. hyo* proteins or polypeptides for use in the vaccine includes, but is not limited to, P46, P65, P85, P97, P102, P70, P50 and P44. These and other *M. hyo* proteins have been described, e.g., in International Patent Publication WO 96/28472 and WO 95/09870, European Patent Publication No. 0 475 185 A1, U.S. Pat. No. 5,788,962, International Patent Publication WO 91/15593, U.S. Pat. No. 5,252,328, King et al. (1997; *Vaccine* 15:25–35), Wilton et al. (1998, *Microbiology* 144:1931–1943), and Hsu et al. (1998, *Gene* 214:13–23).

In another embodiment, the vaccine used in the method of the present invention includes at least one immunogenic fragment of a *M. hyo* protein or polypeptide. In accordance with the present invention, the immunogenic fragments to be included in the vaccine have a sequence of at least about 10 to 20, preferably at least about 30 to 40, or more preferably at least 50 to about 100 contiguous amino acids of a *M. hyo* protein or polypeptide. Preferably, the immunogenic fragment is a fragment of a *M. hyo* protein or polypeptide which includes but not limited to P46, P65, P85, P97, P102. P70, P50 and P44.

Preferably, the *M. hyo* proteins for use in vaccines are substantially pure or homogeneous. For example, a desired *M. hyo* protein or polypeptide can be expressed in host cells transformed with a nucleotide sequence encoding such protein or polypeptide, then purified by a variety of methods well known in the art. See, for example, the techniques described in "Methods In Enzymology", 1990, Academic Press, Inc., San Diego, "Protein Purification: Principles and Practice", 1982, Springer-Verlag, New York. Purified *M. hyo* polypeptides and proteins and immunogenic fragments thereof can also be prepared using known synthetic methods.

In another embodiment, the vaccine for use in the present method includes a *M. hyo* protein, polypeptide, or an immunogenic fragment thereof and at least one other immunogenic or antigenic polypeptide which is not a *M. hyo* protein, polypeptide, or immunogenic fragment thereof and is preferably a viral, bacterial or parasitic polypeptide. In a preferred embodiment the antigen is bovine herpesvirus type 1 (BHV-1), bovine viral diarrhea virus (BVDV), bovine respiratory syncitial virus (BRSV), parainfluenza virus (PI3), *Pasteurella multocida, Haemophilus somnus, Mycoplasma mycoides, Mycoplasma agalactiae, Mycoplasma californicum, Mycoplasma bovirhinis, Mycoplasma dispar, Mycoplasma canis,* or *Manheimia haemolytica.* Such a composition is beneficial as a combination vaccine. The subunit vaccines and combination vaccines of the present invention can be employed in the methods of the present invention to treat or prevent diseases or disorders caused by *M. bovis* infection.

*M. bovis* polypeptides and proteins and immunogenic fragments thereof can also be expressed and delivered using live recombinant viral and bacterial vectors such as adenovirus or Salmonella. The actual vectors are also known and readily available within the art or can be constructed by one skilled in the art using well-known methodology.

Nucleic Acid Vaccines

The vaccination method of the present invention can be practiced using *M. hyo* genes or nucleic acid molecules encoding for *M. hyo* proteins, polypeptides, or immunogenic fragments of such proteins and polypeptides. Such genes and nucleic acids can be prepared using techniques known in the art and administered to an animal to express the encoded protein, polypeptide or fragment thereof in vivo.

In one embodiment, the vaccine used in the present invention includes at least one gene or nucleic acid molecule encoding a *M. hyo* protein such as, but not limited to, P46, P65, P85, P97, P102, P70, P50 and P44.

In another embodiment, the vaccine used in the present invention includes at least one gene or nucleic acid molecule encoding an immunogenic fragment of a *M. hyo* protein or polypeptide. The immunogenic fragments to be included in the vaccine are composed of at least about 10 to 20, or preferably at least about 30 to 40, or more preferably at least about 100 contiguous amino acids of a *M. hyo* protein or polypeptide which includes, but is not limited to, P46, P65, P85, P97, P102, P70, P50 and P44.

The genes or nucleic acid molecules can be administered to an animal by known methods, such as, for example, by use of a gene gun. Further, the genes or nucleic acid molecules can be present in association with liposomes or other transfection facilitating agents, as are known in the art.

Expression Systems

A variety of host-expression vector systems may be utilized to express a *M. hyo* immunogenic protein or polypeptide. Such host-expression systems can be employed to produce and purify the coding sequences of interest, and to express and purify a *M. hyo* protein, polypeptide, or a fragment thereof for use in the vaccination method of the present invention. Typical host-expression systems include but are not limited to microorganisms such as bacteria (e.g., *E. coli, B. subtilis*) transformed with recombinant bacteriophage DNA, plasmid DNA or cosmid DNA expression vectors containing mhp3 coding sequences; yeast (e.g., *Saccharomyces, Pichia*) transformed with recombinant yeast expression vectors containing the *M. hyo* gene product coding sequences; insect cell systems infected with recombinant virus expression vectors (e.g., baculovirus) containing the *M. hyo* coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing *M. hyo* coding sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5 K promoter).

In a preferred embodiment, the expression system is a bacterial system.

Dosing and Modes of Administration

According to the present invention, an effective amount of a *M. hyo* vaccine administered to calves provides effective immunity against a later challenge of *M. bovis*. In one embodiment, the *M. hyo* vaccine is administered to calves at about 7–28 days of age, and more preferably, at about 21 days of age.

In a preferred embodiment, the *M. hyo* vaccine is administered twice to calves. The first administration is performed when the animal is at about 7–28 days of age, preferably 21 days of age. The second administration is performed when the animal is at about 35–49 days of age, preferably about 42 days of age.

The amount of a *M. hyo* vaccine that is effective depends on the ingredients of the vaccine and the schedule of administration. Typically, when inactivated whole cell *M. hyo* preparation is used in a vaccine, an amount of the vaccine containing about $1\times10^6$ to about $5\times10^{10}$ colony forming units (CFU) per dose is effective when administered twice to the animal during a period of about 3 weeks. Preferably, a *M. hyo* bacterin vaccine that provides effective immunity contains about $1\times10^8$ to $5\times10^{10}$ CFU/dose and more preferably, about $5\times10^8$ to $5\times10^{10}$ CFU/dose, when administered twice to the animal during a period of about 3 weeks. The first administration is performed when the animal is at about 7–28 days of age, preferably 21 days of age. The second administration is performed when the animal is at about 35–49 days of age, preferably about 42 days of age.

According to the present invention, when the preferred bacterin product RESPISURE is administered, RESPISURE is administered preferably twice, each time at the amount of about 0.5 to about 5.0 ml, preferably about 1.5 ml to about 2.5 ml, and more preferably, about 2 ml. The first administration is performed when the animal is at about 7–28 days of age, preferably 21 days of age. The second administration is performed when the animal is at about 35–49 days of age, preferably about 42 days of age.

The amount of a *M. hyo* subunit vaccine containing at least one *M. hyo* protein, polypeptide, or an immunogenic fragment thereof is effective when administered twice, each time at about 0.01 μg to about 200 μg per administration. The first administration is performed when the animal is at about 7–28 days of age, preferably 21 days of age. The second administration is performed when the animal is at about 35–49 days of age, preferably about 42 days of age.

The amount of a *M. hyo* vaccine containing genes or nucleic acid molecules (preferably DNA) encoding at least one *M. hyo* protein, polypeptide, or an immunogenic fragment thereof is effective when administered twice, each time at about 0.1 μg to about 200 mg per administration. The first administration is performed when the animal is at about 7–28 days of age, preferably 21 days of age. The second administration is performed when the animal is at about 35–49 days of age, preferably about 42 days of age.

In accordance with the present invention, administration can be achieved by known routes, including the oral, intranasal, mucosal topical, transdermal, and parenteral (e.g., intravenous, intraperitoneal, intradermal, subcutaneous or intramuscular). Administration can also be achieved using needle-free delivery devices. Administration can be achieved using a combination of routes, e.g., first administration using a parental route and subsequent administration using a mucosal route. A preferred route of administration is subcutaneous or intramuscular administration.

The present invention also contemplates a single dose vaccination method, which eliminates the necessity of administration of additional doses to calves in order to generate and/or maintain immunity against *M. bovis.*

The *M. hyo* vaccine administered in accordance with the present invention may include additional components, such as an adjuvant (e.g., mineral gels, e.g., aluminum hydroxide; surface active substances such as lysolecithin; glycosides, e.g., saponin derivatives such as Quil A or GPI-0100; cholesterol, pluronic polyols; polyanions; non-ionic block polymers, e.g., Pluronic F-127; peptides; mineral oils, e.g. Montanide ISA-50, carbopol, Amphigen, Alhydrogel, oil emulsions, e.g. an emulsion of mineral oil such as BayolF/Arlacel A and water, or an emulsion of vegetable oil, water and an emulsifier such as lecithin; alum, cytokines and combinations of adjuvants.).

According to the present invention, the administration of an effective amount of a *M. hyo* bacterin administered to calves at approximately three and six weeks of age provides effective immunity against respiratory infections, including pneumonia and reduces the level of *M. bovis* in the lung.

The present invention provides a method of immunizing a calf against infection by *Mycoplasma bovis* comprising administering to the calf at least one dose, and preferably two doses of the *M. hyo* bacterin so as to immunize the calf against *Mycoplasma bovis* infection. In a preferred embodiment, the bacterin is administered subcutaneously. Moreover, it is preferred that the bacterin dose comprise about 2 ml of the bacterin, each ml containing about $2.5\times10^8$ *M. hyo* CFU. The bacterin is desirably administered twice to the calf; once at about three weeks, and once at about six weeks, after the birth of the calf.

The present invention also contemplates that the administration of an effective amount of a *M. hyo* bacterin administered to animals, and preferably cattle to treat or prevent disorders including pneumonia, arthritis, mastitis, otitis and reproductive disorders in such animals.

The present invention is further illustrated, but not limited by the following examples.

EXAMPLE 1

Materials and Methods

Animals

Healthy crossbred dairy calves at approximately fourteen days of age were obtained for vaccination. Calves were acclimatized for seven days prior to the initiation of the study. All calves received a concentrated non-medicated diet daily, free of any known contaminants or pesticides and had free access to water.

Vaccines

The bacterin which was used to vaccinate calves contained a BEI inactivated whole cell *M. hyo* bacteria at an appropriate concentration per dose. In addition, the vaccine preparation contained phosphate buffered saline (PBS) and an oil in water adjuvant. The placebo contained PBS.

Challenge Method

Each calf received 12 ml of a fresh *M. bovis* culture (approximately $1\times10^8$ to $1\times10^{10}$ colony forming units (CFU/ml)) by the intranasal route on three consecutive days. A viable count (CFU/ml) of the challenge inoculum was determined shortly after the completion of each experimental challenge.

Experimental Procedure

A unique ear tag number identified each calf. Animals were randomly assigned by age into pens and treatment groups.

Animals were vaccinated with either 2.0 ml of the vaccine or 2.0 ml of the placebo by the subcutaneous route on day 0 (left neck) and on day 21 (right neck).

Rectal temperatures were measured each morning 1-day prior to challenge, immediately prior to challenge, and for 20 days following challenge.

All animals were necropsied at approximately 3 weeks following the experimental *M. bovis* challenge. Calves were euthanized and all major organs, excluding the central nervous system, were examined grossly.

Lungs were removed and evaluated grossly for characteristic lesions attributable to a *M. bovis* infection. Lesions were sketched on a standard lung diagram. Percent gross involvement per each lung lobe was weighted using the following ratios of individual lung lobes to total lung mass.

| Lung Lobe | Percentage of Lung |
|---|---|
| Left Apical | 5 |
| Right Apical | 6 |
| Middle | 5 |
| Left Cardiac | 6 |
| Right Cardiac | 7 |
| Accessory | 4 |
| Left Diaphragmatic | 32 |
| Right Diaphragmatic | 35 |

The weighted lung lobe values were then summed in order to determine the percentage of total lung with gross lesions (Pointon et al, 1992). In addition the following formula was used to calculate the percent reduction.

$$100 - \frac{\text{Mean Percent Lung Damage of Treatment Group}}{\text{Mean Percent Lung Damage of Control Group}} = \text{Percent Reduction}$$

In addition, each lung was lavaged with 50 ml of PBS. Attempts were made to isolate and determine the viable *M. bovis* counts from the bronchial lavage fluid. The *M. bovis* viable count (CFU/ml) was determined by preparing appropriate serial dilutions of bronchial lavage fluid and plating samples onto an appropriate agar medium.

EXAMPLE 2

In this example, the efficacy of a *M. hyo* bacterin was evaluated in young calves. Thirty healthy crossbred calves were randomly assigned by age.

Animals were vaccinated with 2 ml of either the vaccine or placebo by the subcutaneous route on day 0 (left neck) and on day 21 (right neck). The experimental treatment groups and vaccines used are shown in Table 1.

TABLE 1

Experimental Treatment Groups

| Treatment Group | Experimental Vaccines (2 ml dose) | Number of Animals |
|---|---|---|
| A | *M. hyo* ($5\times10^8$ CFU) + Amphigen | 15 |
| B | Placebo (PBS) | 15 |

Calves were challenged as described above at 3 weeks following second vaccination. Each calf received 12 ml of a fresh *M. bovis* culture by the intranasal route on three consecutive days.

A viable count (CFU/ml) of each challenge inoculum was determined within one hour after the completion of the *M. bovis* experimental challenge. Results are shown in Table 2.

TABLE 2

| Viable Count (CFU/ml) of *Mycoplasma bovis* Challenge Inoculum | |
|---|---|
| Challenge Culture | CFU/ml |
| Day 1 | $2.2 \times 10^9$ |
| Day 2 | $3.2 \times 10^9$ |
| Day 3 | $1.7 \times 10^9$ |

Rectal temperatures were measured each morning 1 day prior to challenge immediately prior to challenge, and for 20 days following experimental *M. bovis* challenge. Results are summarized in FIG. 1. Calves vaccinated with the *M. hyo* bacterin (Treatment Group A) had lower mean body temperatures on day 7, days 9 through 18, and day 20 when compared to the placebo vaccinated animals (Treatment Group B).

All animals were necropsied at approximately 3 weeks following the experimental *M. bovis* challenge. Lungs were removed and evaluated grossly for characteristic lesions attributable to a *M. bovis* infection. Percent lung damage scores and percent reduction of lung lesions are summarized in Table 3. Animals in Treatment Group A (*M. hyo* bacterin) had a 45.1 percent reduction in gross lung lesions when compared to the placebo group (Treatment Group B).

TABLE 3

Summary of Percent Lung Damage Scores
Mean Weighted Percentage ± Standard Deviation

| Treatment Group | Percent Lung Damage | Percent Reduction |
|---|---|---|
| A | 4.17 ± 8.90 | 45.1 |
| B | 7.60 ± 15.93 | — |

Each lung was lavaged with 50 ml of pas. Results of the isolation of *M. bovis* from bronchial lavage samples approximately twenty-one days following the experimental *M. bovis* challenge are summarized in Table 4. Calves in the *M. hyo* bacterin vaccinated group (Treatment Group A) had reduced levels of viable *M. bovis* isolated from lung lavage samples when compared to the placebo group (Treatment Group B).

TABLE 4

| Summary of *Mycoplasma bovis* Isolations from Lung Lavage Fluid | |
|---|---|
| Treatment Group | CFU/ml |
| A | $2.68 \times 10^6$ |
| B | $4.50 \times 10^6$ |

In conclusion, calves that were vaccinated two times with the *M. hyo* bacterin (Treatment Group A) had a reduction in gross lung lesions, reduced rectal temperatures, and a reduced level of viable *M. bovis* isolated from lung lavage samples when compared to the placebo vaccinated group (Treatment Group B). The results indicate that vaccination with a *M. hyo* bacterin offers cross-protection from an experimental *M. bovis* challenge in cattle.

What is claimed is:

1. A method of treating or preventing a disease or disorder in an animal caused by infection with *Mycoplasma bovis* comprising administering to the animal at least $5\times10^8$ CFU of BEI inactivated whole cell *Mycoplasma hyopneumoniae* bacterin in PBS and an oil in water adjuvant.

2. The method according to claim 1 wherein said animal is a bovine.

3. The method according to claim 1 wherein said animal is a calf.

4. The method of claim 1 wherein the amount of said bacterin administered is from about 0.5 to about 5.0 ml.

5. The method of claim wherein 4 wherein the amount of said bacterin administered is from about 1.5 ml to about 2.5 ml.

6. The method of claim 5 wherein the amount of said bacterin administered is about 2 ml.

7. The method of claim 1 wherein the bacterin is administered subcutaneously or intramuscularly.

8. The method according to claim 1 wherein the *Mycoplasma hyopneumoniae* bacterin further comprises at least one protein from *Mycoplasma hyopneumoniae* or an immunogenic fragment thereof.

9. The method according to claim 8 wherein said protein is selected from the group consisting of P46, P65, P85, P97, P102, P70, P50 and P44.

10. The method of claim 8 wherein said protein, polypeptide or said immunogenic fragment is recombinantly produced.

11. The method according to claim 7 where about 0.5 ml to 5.0 ml of said *Mycoplasma hyopneumoniae* bacterin is administered to the animal.

12. The method according to claim 7 wherein said *Mycoplasma hyopneumoniae* bacterin is administered 2.0 ml.

13. The method according to claim 1 wherein the *Mycoplasma hyopneumoniae* bacterin further comprises a nucleotide sequence encoding at least one protein or polypeptide from *Mycoplasma hyopneumoniae* or an immunogenic fragment of said protein.

14. The method according to claim 13 wherein said protein is selected from the group consisting of P46, P65, P85, P97, P102, P70, P50 and P44.

15. The method according to claim 13 where about 0.5 ml to 5.0 ml of said *Mycoplasma hyopneumoniae* bacterin is administered to the animal.

16. The method according to claim 13 wherein said *Mycoplasma hyopneumoniae* bacterin is administered 2.0 ml.

17. The method according to claim 1 wherein the *Mycoplasma hyopneumoniae* bacterin further comprises an adjuvant.

18. The method according to claim 11 wherein the adjuvant is selected from the group consisting of: Quil A, saponin, GPI-0100, cholesterol, DDA, aluminum gel, carbopol, lecithin and oil blend, aluminum hydroxide oil in water, water in oil, cytokines, or combinations of adjuvants.

19. The method according to claim 11 wherein the *Mycoplasma hyopneumoniae* bacterin further comprises a viral or bacterial respiratory, enteric, or reproductive pathogen antigens.

20. The method according to claim 19 wherein said respiratory antigens are selected from the group consisting of bovine herpesvirus type 1 (BHV-1), bovine viral diarrhea virus (BVDV), bovine respiratory syncitial virus (BRSV), parainfluenza virus (PI3), *Pasteurella multocida, Haemophilus somnus, Mycoplasma mycoides, Mycoplasma agalactiae, Mycoplasma califomicum, Mycoplasma bovirhinis, Mycoplasma dispar, Mycoplasma canis,* and *Manheimia haemolytica.*

21. The method according to claim 1 wherein the *Mycoplasma hyopneumoniae* bacterin further comprises a pharmaceutically acceptable carrier.

22. The method according to claim 1 wherein the *Mycoplasma hyopneumoniae* bacterin is administered to the animal at about 21 days of age.

23. The method according to claim 1 wherein the *Mycoplasma hyopneumoniae* bacterin is administered to the animal at about 21 days of age, followed by a second administration at about 42 days of age.

24. A method of treating or preventing a disease or disorder in an animal caused by infection with *Mycoplasma bovis* comprising administering to the animal at least $5\times10^8$ CFU of BEI inactivated whole cell *Mycoplasma hyopneumoniae* bacterin in PBS and an oil in water adjuvant.

25. A method for treating or preventing a disease or disorder having the clinical manifestations of pneumonia of calves, which is often accompanied by arthritis, also known as pneumonia-arthritis syndrome, by administering to the calves at least $5\times10^8$ CFU of BEI inactivated whole cell *Mycoplasma hyopneumoniae* bacterin in PBS and an oil in water adjuvant.

* * * * *